United States Patent
Klomp

(10) Patent No.: US 11,235,097 B2
(45) Date of Patent: Feb. 1, 2022

(54) PRESSURE REGULATION SYSTEM

(71) Applicant: FRITZ RUCK OPHTHALMOLOGISCHE SYSTEME GMBH, Eschweiler (DE)

(72) Inventor: Manfred Klomp, Hulsberg (NL)

(73) Assignee: FRITZ RUCK OPHTHALMOLOGISCHE SYSTEME GMBH, Eschweiler (DE)

( * ) Notice: Subject to any disclaimer, the term of this patent is extended or adjusted under 35 U.S.C. 154(b) by 380 days.

(21) Appl. No.: 16/330,910

(22) PCT Filed: Aug. 10, 2017

(86) PCT No.: PCT/EP2017/070344
§ 371 (c)(1),
(2) Date: Mar. 6, 2019

(87) PCT Pub. No.: WO2018/046225
PCT Pub. Date: Mar. 15, 2018

(65) Prior Publication Data
US 2019/0231968 A1    Aug. 1, 2019

(30) Foreign Application Priority Data
Sep. 6, 2016 (EP) .................................. 16187313

(51) Int. Cl.
*A61M 3/02* (2006.01)
*A61M 1/00* (2006.01)
(Continued)

(52) U.S. Cl.
CPC ........ *A61M 3/0254* (2013.01); *A61M 1/0058* (2013.01); *A61M 3/0216* (2014.02);
(Continued)

(58) Field of Classification Search
CPC ................ A61M 5/145; A61M 5/1452; A61M 5/14526; A61M 5/14586; A61M 5/14593;
(Continued)

(56) References Cited

U.S. PATENT DOCUMENTS 6,491,661 B1    12/2002   Boukhny et al.
8,348,107 B2 *  1/2013    Succar ............... B65D 83/0094
                                              222/401

(Continued)

FOREIGN PATENT DOCUMENTS

EP          1897572 A1     3/2008

OTHER PUBLICATIONS

International Search Report dated Oct. 5, 2017 from International Patent Application No. PCT/EP2017/070344, filed Aug. 10, 2017.
(Continued)

*Primary Examiner* — Nathan R Price
*Assistant Examiner* — Anna E Goldberg-Richmeier
(74) *Attorney, Agent, or Firm* — Workman Nydegger

(57) ABSTRACT

A pressure regulation system for discharging a liquid having a predetermined liquid pressure from a liquid opening, including an elastic bag having a liquid phase and a gas phase, where the liquid opening in an operational position of the elastic bag is formed in the lower area of the elastic bag, at least two push elements, at least one drive unit and a control unit. The elastic bag has a gas opening, which extends into the gas phase. The pressure regulation system has a ventilation unit, which is connected to the control unit for communication and which connects to the gas opening of the elastic bag. The ventilation unit regulates the liquid pressure of the liquid discharged through the liquid opening by means of a gas supply into the elastic bag and/or a gas discharge from the elastic bag.

10 Claims, 3 Drawing Sheets

(51) Int. Cl.
*A61M 5/168* (2006.01)
*A61M 5/152* (2006.01)
(52) U.S. Cl.
CPC ...... *A61M 3/0233* (2013.01); *A61M 5/16804* (2013.01); *A61M 5/152* (2013.01); *A61M 2205/0216* (2013.01); *A61M 2205/3331* (2013.01); *A61M 2205/3379* (2013.01); *A61M 2210/0612* (2013.01)
(58) Field of Classification Search
CPC .. A61M 5/148; A61M 5/1483; A61M 5/1486; A61M 5/152; A61M 5/155; A61M 2005/14513; A61M 3/0216; A61M 3/0233; B01L 3/50273; F04B 43/02; F04B 43/0733; B65D 35/28
See application file for complete search history.

(56) References Cited

U.S. PATENT DOCUMENTS

| | | |
|---|---|---|
| 2014/0100518 A1 | 4/2014 | Baxter et al. |
| 2014/0276639 A1 | 9/2014 | Tarkeshian et al. |

OTHER PUBLICATIONS

International Preliminary Report on Patentability of PCT/EP2017/070344 dated Mar. 12, 2019.

\* cited by examiner

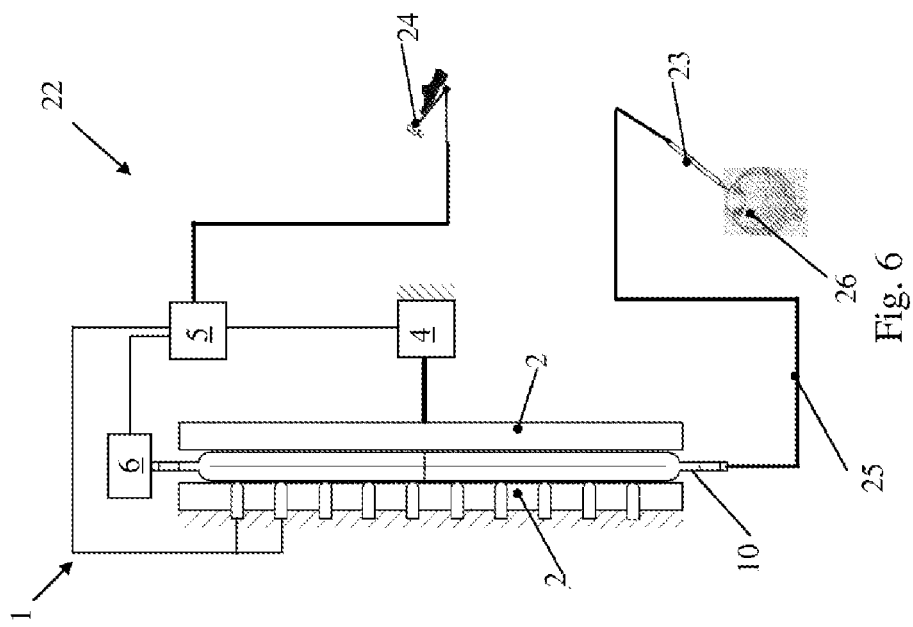
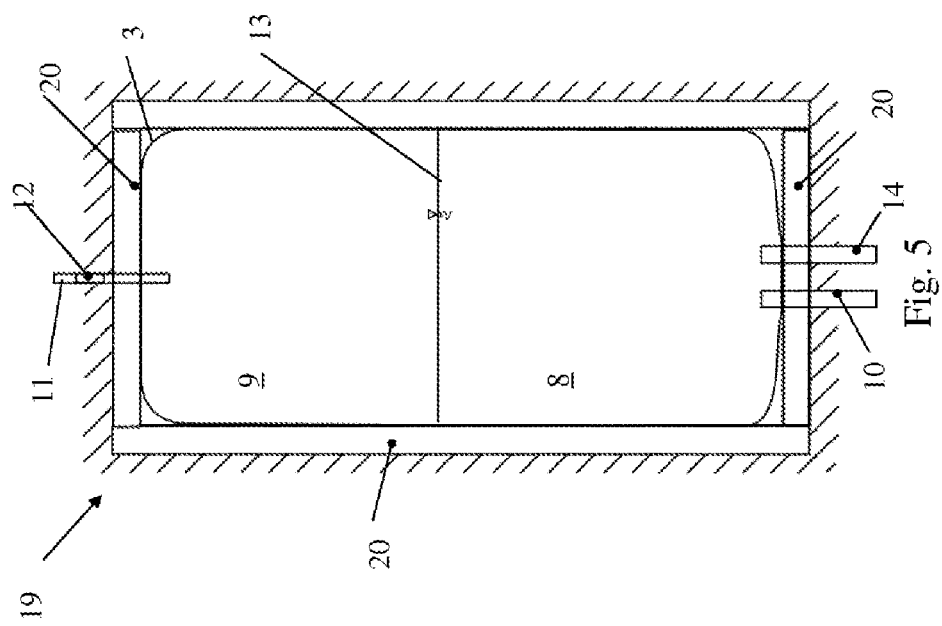

PRESSURE REGULATION SYSTEM

The present application is a U.S. National Stage of International Application No. PCT/EP2017/070344, filed on Aug. 10, 2017, designating the United States and claiming the priority of European Patent Application No. 16187313.8 filed with the European Patent Office on Sep. 6, 2016. All of the aforementioned applications are incorporated herein in their respective entireties by this reference.

FIELD OF THE INVENTION

The invention relates to a pressure regulation system for discharging a liquid having a predetermined liquid pressure from a liquid opening, comprising an elastic bag having a liquid phase and a gas phase, wherein in the operational position of the elastic bag there is formed the liquid opening in the lower area of the elastic bag, at least two push elements, which abut at opposite walls of the elastic bag, at least one drive unit, which is configured to drive at least one push element, wherein the at least two push elements may be moved towards one another by driving at least one push element, and a control unit, which is configured to communicate with the at least one drive unit.

BACKGROUND

The publication U.S. Pat. No. 6,491,661 B1 discloses a pressure regulation system for an ophthalmic surgery device, which includes an elastic bag, two push elements in the form of plates, two springs, one valve, one pressure sensor and two drive units. The elastic bag is connected to the valve via attachment to a liquid opening of the elastic bag via a flexible hose. One of the plates is movably mounted, and the other plate is fixed using additional elements not explained in greater detail, wherein the two drive units are configured to drive the movably mounted plate. The plates are arranged in parallel to another and abut at opposite walls of the elastic bag, whereby the elastic bag is clamped between the plates. By reducing a distance between the plates by driving the movably mounted plate by means of two drive units, a pressure in the bag and, consequently, a liquid pressure, at which liquid is discharged from the elastic bag, may be increased, wherein by means of the pressure sensor and an integrated controller, a predetermined pressure may be maintained in the elastic bag. The pressure regulation system further has a volume flow sensor, which measures a discharge rate of liquid from the elastic bag, whereby an amount of the liquid already discharged from the elastic bag may be calculated.

With the pressure regulation system known from the publication U.S. Pat. No. 6,491,661 B it has been proven to be disadvantageous that, in plane elastic bags, the liquid pressure, at which the liquid is discharged from the elastic bag, may be regulated very poorly. Even a small reduction of the distance between the plates will lead to a large pressure change. In particular in the medicinal surgical field, fine tuning of a liquid pressure discharged by a pressure regulation system is absolutely essential in order to keep surgical risks as low as possible.

It is the task of the present invention to provide a pressure regulation system, wherein the liquid pressure, at which the liquid is discharged from the elastic bag, may be regulated in a better way.

Aspects of Some Example Embodiments

According to the invention, this task is solved by the elastic bag having a gas opening, which extends into the gas phase, and by the pressure regulation system having a ventilation unit, which is connected to the control unit for communication and which is adjacent to the gas opening of the elastic bag, wherein the ventilation unit regulates a liquid pressure of a liquid discharged by the liquid opening by means of a gas supply into the elastic bag and/or a gas discharge from the elastic bag.

In this way, there is obtained the advantage that the liquid pressure, at which the liquid is pushed out of the elastic bag, may be regulated independently of a pressure, which is exerted by the plates moving towards one another onto the gas phase and the liquid phase in the elastic bag. The pressure in the elastic bag and, hence, the liquid pressure of the liquid is merely regulated by the ventilation unit via a gas supply into the elastic bag and/or a gas discharge from the elastic bag, wherein a volume of the elastic bag is reduced and, consequently, also a volume of the gas phase in the elastic bag is reduced by the plates being moved towards one another. Due to a small volume of the gas phase, the liquid pressure at the liquid opening will rather quickly adapt to the pressure change in the elastic bag conditioned by the gas supply into the elastic bag and/or the gas discharge from the elastic bag. By regulating the pressure within the bag via the ventilation unit, the liquid pressure may be regulated rather finely, and due to keeping the volume of the gas phase small, the pressure regulation system will react very quickly. The control unit advantageously detects the amount of liquid, which is discharged from the elastic bag per second, by means of the pressure in the elastic bag and by means of an opening cross-section of the liquid opening.

The elastic bag preferably has an essentially planar shape. Especially preferably the elastic bag is formed from a plastic film, which is folded over and which is sealed at the edges thereof. In this way there is obtained the advantage that the push elements, which advantageously also have a planar shape and are preferably formed by plates, abut in a planar way at the walls of the elastic bag. An area of the plates, via which the plates abut at the walls of the elastic bag, is usefully the same as or larger than areas of the walls. The plates are arranged preferably in parallel to one another and in parallel to the elastic bag. In this way there is obtained the advantage that, if the plates move towards one another, then the entire elastic bag will be compressed and bulges of the elastic bag may be greatly prevented. There is further given the advantage that the elastic bag may be emptied completely, apart from some smaller residues, thus preventing unnecessary waste of liquid.

The gas opening is preferably formed by a first tube, which in the operational position of the elastic bag projects from an upper side of the elastic bag into the gas phase or which in the operational position of the elastic bag projects from a lower side of the elastic bag into the gas phase. The liquid opening is advantageously formed by a second tube. By the gas opening and the liquid opening being formed as tubes, these may be very easily, in the case of an elastic bag formed from a plastic film that is folded over and sealed at the edges, put between the folded-over plastic film and sealed therewith during production. If the first tube projects from a lower side of the elastic bag into the gas phase, there will be given the advantage that the gas opening and the liquid opening are arranged on one side, namely in the operational position of elastic bag, at the lower side of the elastic bag, whereby handling of the elastic bag will be facilitated.

The gas opening and/or the liquid opening each usefully have a protection against break, wherein the gas opening and the liquid opening are released only upon cracking of the respective protection against break. In this way there is given the advantage that, on the one hand side, the intactness of the bag and the content thereof may be immediately examined and, on the other side, an inadvertent opening the elastic bag may be prevented. In this connection, it is also advantageous to equip the liquid opening and/or the gas opening with a Luer connection, whereby the elastic bag may be easily connected to another medicinal device or medicinal elements.

The pressure regulation system advantageously has extensions elements, wherein the elastic bag may be extended transversely to a movement of the at least one push element by means of the extension elements, when the push elements are moved towards one another. Extension elements may, for example, be springs, actuators, ropes having weights, etc. By means of the extension elements, the elastic plastic bag is stretched, whereby a collapse thereof due to gravity may be prevented and an optimal functioning of the pressure regulation system may be ensured at any time.

In a preferred embodiment the pressure regulation system has side walls, which each laterally abut the plates in order to enclose the elastic bag. The side walls may be configured to be rigid, wherein the push elements move along the side walls, when the push elements move towards one another, or the side walls may also be configured to be slidable into one another, similarly to a telescopic rod. By the provision of side plates, there is obtained the advantage that in the case of high pressures, a disproportionally high extension in the lateral direction, in particular bulging, of the elastic bag is being prevented, whereby the liquid pressure may also be regulated well in the case of high pressures.

In a further preferred embodiment the pressure regulation system has at least one sensor, wherein the at least one sensor is configured to detect a liquid level between gas phase and liquid phase and wherein it is arranged at a pressure element or applied to the elastic bag. In this way, there is given the advantage that by way of the control unit, on the basis of data of the sensor, the amount of liquid still present in the elastic bag may be very exactly determined.

BRIEF DESCRIPTION OF THE DRAWINGS

Further advantageous embodiments of the pressure regulation system according to the invention will be explained in greater detail in the following by way of the figures.

The FIGS. 1 and 2 show a first embodiment of the pressure regulation system according to the invention, respectively in a schematic side view.

Figure 4:
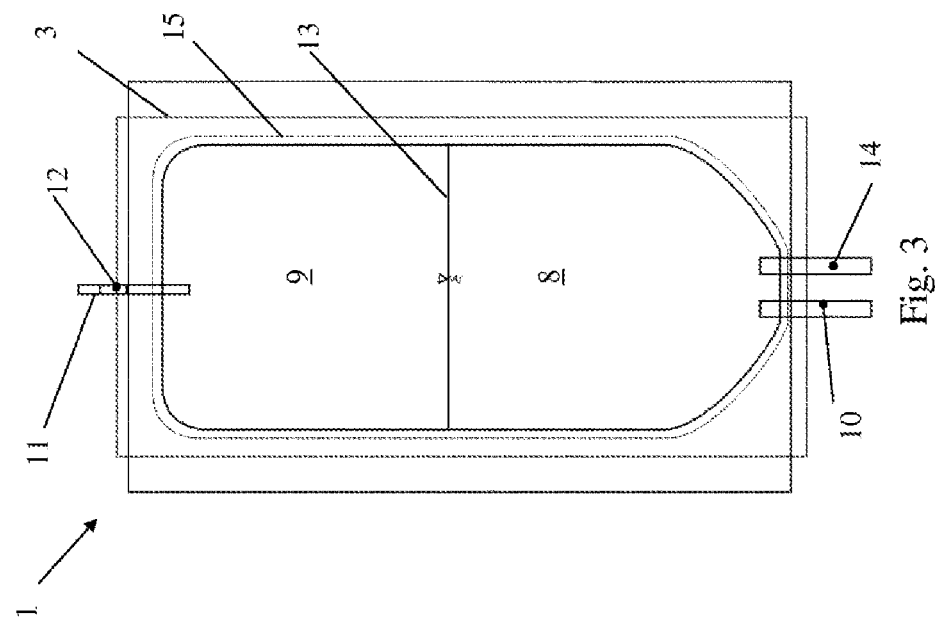

The FIGS. 4 and 5 each show a further embodiment of the pressure regulation system according to the invention in a schematic side view.

Figure 1:
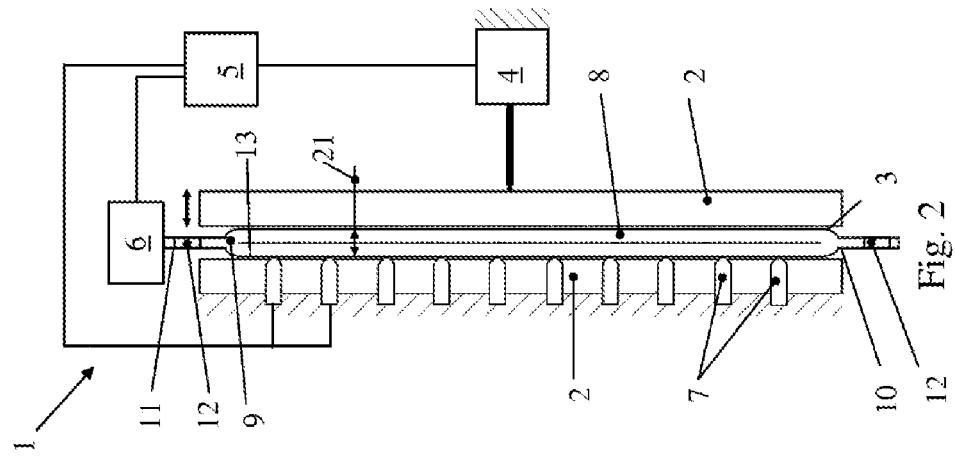

FIG. 6 shows the pressure regulation system according to the invention according to FIG. 1 when used in an ophthalmic surgery device in a schematic illustration.

DETAILED DESCRIPTION OF SOME EXAMPLE EMBODIMENTS

Figure 2:
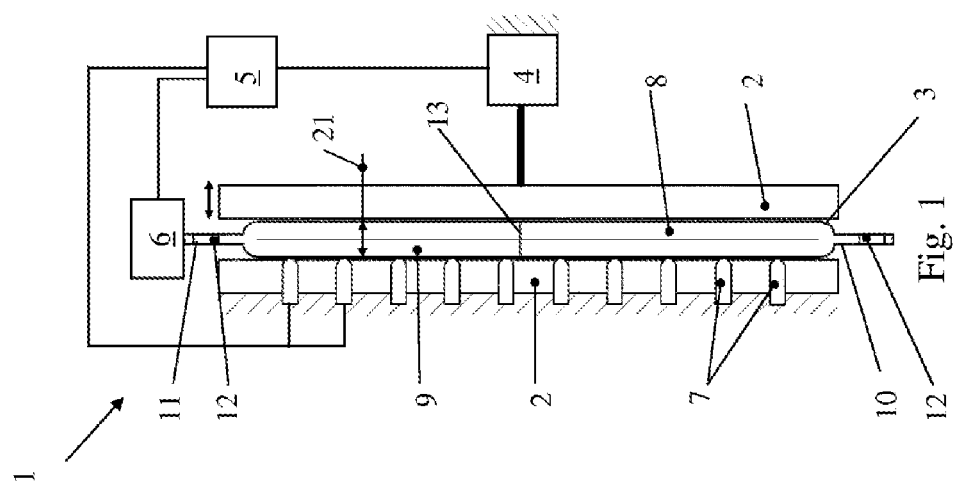
Figure 3:
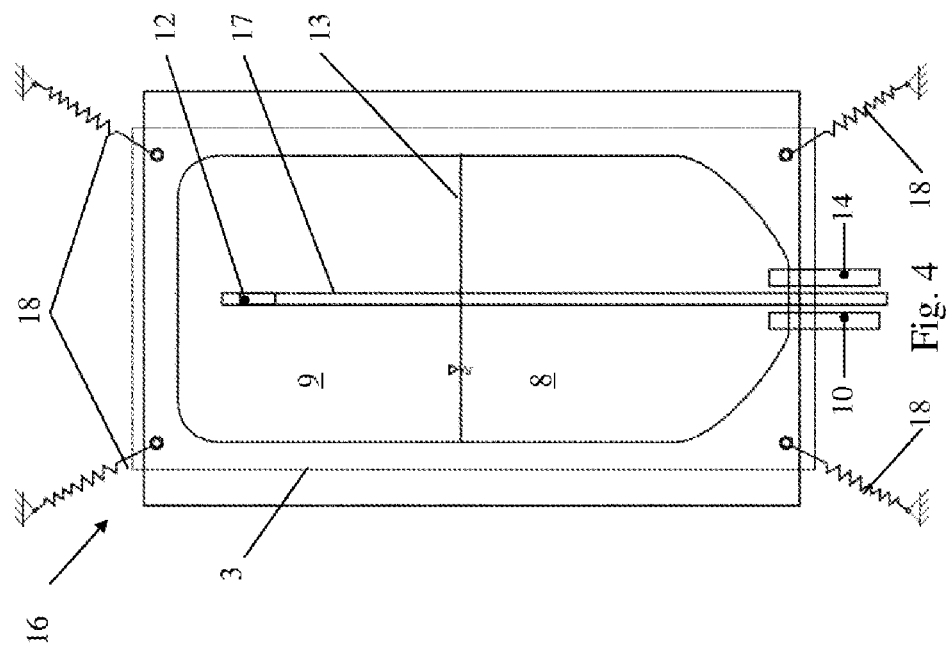
FIG. 3 shows the first embodiment of the pressure regulation system according to the invention according to FIG. 1 in a schematic side view.

The FIGS. 1 and 2 show a first embodiment of the pressure regulation system 1 according to the invention respectively in a schematic side view. The pressure regulation system 1 comprises two push elements formed by plates 2, an elastic bag 3, a drive unit 4, a control unit 5, a ventilation unit 6 and ten sensors 7. The elastic bag 3 has a liquid phase 8 and a gas phase 9, and in its operational position it is oriented vertically. A liquid of the liquid phase 8 may, for example, be formed by infusion liquid, in particular saline, or irrigation liquid. A gas of the gas phase 9 is advantageously formed by air. The elastic bag 3 has in the lower area an injection opening and a liquid opening, which liquid opening is formed by a second tube 10 and through which liquid may be discharged from the liquid phase 8 of the elastic bag 3. The injection opening is illustrated in FIG. 3 and serves for injecting liquid or additives, which are to be added to the liquid in the elastic bag 3, for example before the beginning of a surgical intervention. The injection opening is formed by a third tube 14. In the upper area of the elastic bag 3 there is formed a gas opening, which gas opening is formed by a first tube 11. The first tube 11 extends into the gas phase 9 of the elastic bag 3 and is connected to the ventilation unit 6.

The plates 2 are arranged in parallel and in a distance to one another, respectively abutting at the opposite walls of the elastic bag 3. Consequently, the elastic bag 3 is arranged clamped between the plates 2. One plate 2 is fixed, and the other plate 2 is movably mounted, wherein the movably mounted plate 2 may be driven by the drive unit 4 such that the plates 2 may be moved towards one another, whereby a distance 21 between the plates 2 may be reduced. The drive unit 4 is advantageously formed by a rack and pinion drive unit that is driven by an electric motor, a threaded bar drive that is driven by an electric motor, a pneumatically driven cylinder or a hydraulically driven cylinder.

The sensors 7 as well as the ventilation unit 6 and the drive unit 4 are connected to the control unit 5 for communication. For clarity reasons, not all ten sensors 7 are connected to the control unit 5 in the FIGS. 1 and 2. The sensors 7 are formed by optical sensors, wherein these will emit a sensor signal, indicating the detection of liquid, if the probe tips thereof abut at the bag 3 in the area of the liquid phase 8. Such optical sensors are known to those skilled in the art. The sensors 7 are arranged on a plate 2 in equal intervals to one another such that when the pressure regulation system 1 is in an operational position as shown in FIGS. 1 and 2, the sensors 7 are arranged along a vertical axis. Consequently, a liquid level 13 in the elastic bag 3 may be detected by the control unit 5 using the sensors 7.

The ventilation unit 6 comprises a proportional pressure valve and a compressor unit for compressing ambient air.

In the first tube 11 as well as in the second tube 10 and the third tube 14, there are respectively formed protections against break 12, wherein the tubes 10, 11 and 14 will only be released for use in a surgical intervention if the protections against break 12 have been cracked.

In the following there is described in greater detail the functional mode of the pressure regulation system 1 according to the invention, wherein an elastic bag 3 that is fully filled with the liquid is assumed. For this purpose, there was arranged a newly filled elastic bag 3 between the plates 2, or an elastic bag 3 that has already been arranged between the plates 2 is filled with the liquid by means of an auxiliary device via the third tube 14.

By means of the proportional pressure valve of the ventilation unit 6, a pressure in the elastic bag 3 is regulated by a gas supply into the elastic bag 3 and/or a gas discharge from the elastic bag 3 that is controlled by the control unit 5. The pressure in the elastic bag 3 is thereby advantageously adjusted directly at the control unit 5. The liquid pressure in the second tube 10, due to the weight of the liquid, is slightly higher than the pressure adjusted by the proportional pressure valve in the elastic bag 3, wherein a pressure that is lower than an ambient pressure may be applied onto the elastic bag 3 temporarily by the ventilation unit 6 in order to prevent undesired leakage from the second tube 10. By providing an additional valve, connected to the second tube 10, this function may be omitted. With the pressure regulation system 1, the discharge of liquid is only controlled by the ventilation unit 6, wherein already a slightly higher pressure than the ambient pressure or a pressure equal to the ambient pressure, depending on the amount of liquid in the elastic bag 3, will be sufficient in order to discharge liquid from the elastic bag 3. The sensors 7 continuously detect the liquid level 13 during the discharge of liquid from the second tube 10, wherein, if it dips below a predetermined liquid level 13, the control unit 5 controls the drive unit 4 to move the plates 2 towards one another in order to reduce the distance 21 between the plates 2. By moving the plates 2 towards one another, a volume of the elastic bag 3 is reduced, and as a consequence a volume of the gas phase 9 is reduced.

With the system 1 according to the invention depicted in FIG. 1, the liquid level 13 has dropped to the half thereof, and the elastic bag 3 is only half filled. With the system 1 according to the invention depicted in FIG. 2, the distance 21 between the plates 2 in respect to the distance 21 according to FIG. 1 has been reduced by half, whereby the liquid level 13 has again risen to the top of the elastic bag 3. If the liquid level 13 then again drops to the half thereof, the elastic bag 3 will only be filled with a quarter of the original amount of liquid. This process is continued until the elastic bag 3 is empty or until the elastic bag 3 has been emptied to a predetermined amount.

The control unit 5, by knowing the distance 21 between the plates 2 and the position of the liquid level 13 measured by the sensors 7, is configured to detect the amount of liquid present in the elastic bag 3, wherein measurement accuracy of the amount of liquid present will increase with the distance 21 being reduced. Moving the plates 2 towards one another and the reduction of the distance 21 between the plates 2 as a result thereof results not only in a reduction of the volume of the gas phase 9, whereby inertia of the system 1 in the case of pressure changes will be prevented, but rather in an increase of the measurement accuracy of the amount of liquid, which is still present in the elastic bag 3, with a constant number of sensors 7.

In a further embodiment the sensors 7 are formed by capacitive sensors, wherein respectively one capacitive sensor has two sensor elements, which are each attached opposite to another at the plates 2.

FIG. 3 shows the first embodiment of the pressure regulation system 1 according to the invention according to FIG. 1 in a schematic sectional view. The elastic bag 3 consists of an one-piece plastic film which is folded over and sealed at the edges 15 of the plastic film.

FIG. 4 shows a further embodiment of the pressure regulation system 16 according to the invention in a schematic front view. The pressure regulation system 16 differs from the pressure regulation system 1 shown in the FIGS. 1 to 3 in so far as it has extension elements in the form of springs 18. Using the springs 18, the elastic bag 3 is extended transversely to the movement of the movably mounted plates 2, when the plates 2 move towards one another, whereby collapsing or folding of the elastic bag 3 will be prevented, with this keeping essentially its form.

In the pressure regulation system 16 a first tube 17 forming the gas opening further extends from a lower side of the elastic bag 3 into the gas phase 9. In this way there is obtained the advantage that all connections are arranged on one side of the elastic bag 3.

FIG. 5 shows a further embodiment of the pressure regulation system 19 according to the invention in a schematic front view. The system 19 differs from the pressure regulation system 1 shown in FIG. 1 in that the pressure regulation system 19 has side walls 20. The side walls 20 are each fixed at auxiliary elements, in particular a frame, and they are formed by further plates, wherein the driven plate 2 may move in relation to the further plates. This gives the advantage that lateral deflection of the elastic bag 3 or bulging of the elastic bag 3 will be prevented also in the case of high pressures, wherein the liquid pressure may also be well-regulated in the case of high pressures, not resulting in inertia of the system 19 due to the expansion of the elastic bag 3.

FIG. 6 shows the pressure regulation system 1 according to the invention according to FIG. 1 when used in an ophthalmic surgical device 22 in a schematic illustration. The ophthalmic surgical device 22 additionally to the pressure regulation system 1 comprises a surgical tool holder 23 and a control device 24, wherein the surgical tool holder 23 is connected by way of a hose 25 directly to the second tube 10 and has a control valve not depicted. The control valve may, for example, be formed by a magnetic valve. The control device 24 is formed by a foot pedal, which is connected to the control unit 5 for communication. By means of the control device 24, the pressure within the elastic bag 3, and resulting thereof an irrigation pressure, may be changed, by means of which the liquid in the elastic bag 3 may be discharged via the surgical tool holder 23 to an eye 26.

During the entire ophthalmic surgery on the eye 26, the pressure in the elastic bag 3, in particular also in the case of a change in the distance 21 between the plates 2, is advantageously kept constant by the ventilation unit 6.

In a further embodiment, pressure regulation in the elastic bag 3 is only realized if the plates 2 stand still. If the distance 21 between the plates 2 is changed, the regulation of pressure as well as the retrieval of liquid from the elastic bag 3 will be interrupted. In this embodiment, a change in the distance 21 of the plates 2 will preferably be used in order to minimize the gas volume, if a surgeon puts the ophthalmic surgery device 22 down, thus temporarily interrupting the surgical intervention.

In a further embodiment the ventilation unit 6 is formed by a valve controllable by the control unit 5.

The invention claimed is:

1. A pressure regulation system for discharging a liquid having a predetermined liquid pressure from a liquid opening, comprising an elastic bag having a liquid phase and a gas phase, wherein the liquid opening in an operational position of the elastic bag is formed in a lower area of the elastic bag, at least two push elements, which abut at opposite walls of the elastic bag, at least one drive unit, which is configured to drive at least one push element, wherein the at least two push elements are capable of being moved towards one another by driving at least one push element, and a control unit, which is connected to the at least one drive unit for communication, wherein the elastic bag has a gas opening, which extends into the gas phase, and that the pressure regulation system has a ventilation unit, which is connected to the control unit for communication and which connects to the gas opening of the elastic bag, wherein the ventilation unit regulates the liquid pressure of the liquid discharged through the liquid opening by a gas supply into the elastic bag and/or a gas discharge from the elastic bag.

2. The pressure regulation system according to claim 1, wherein a pressure in the elastic bag is kept constant by the ventilation unit in the case of the push elements moving towards one another.

3. The pressure regulation system according to claim 1, wherein the elastic bag has an essentially planar shape.

4. The pressure regulation system according to claim 1, wherein the elastic bag is formed from a plastic film that is folded over, which is sealed at the edges thereof.

5. The pressure regulation system according to claim 1, wherein the gas opening is formed by a first tube, which in the operational position of the elastic bag projects from an upper side of the elastic bag into the gas phase or which in the operational position of the elastic bag projects from a lower side of the elastic bag into the gas phase.

6. The pressure regulation system according to claim 1, wherein the gas opening and/or the liquid opening have a Luer connection.

7. The pressure regulation system according to claim 1, wherein the pressure regulation system has extension elements that are operable to extend the elastic bag transversely to a movement of the at least one push element when the push elements move towards one another.

8. The pressure regulation system according to claim 1, wherein the at least two push elements are formed by plates, which are arranged in parallel to one another.

9. The pressure regulation system according to claim 8, wherein the pressure regulation system has side walls, which each laterally abut the plates in order to enclose the elastic bag.

10. The pressure regulation system according to claim 1, wherein the pressure regulation system has at least one sensor, wherein the at least one sensor is configured to detect a liquid level between gas phase and liquid phase and is arranged on a push element or applied onto the elastic bag.

* * * * *